US00PP33722P2

(12) United States Plant Patent
Thompson

(10) Patent No.: US PP33,722 P2
(45) Date of Patent: Dec. 7, 2021

(54) RASPBERRY PLANT NAMED 'PBB 1473'

(50) Latin Name: ***Rubus idaeus* L.**
Varietal Denomination: PBB 1473

(71) Applicant: Pacific Berry Breeding, LLC, Salinas, CA (US)

(72) Inventor: Ellen Thompson, Watsonville, CA (US)

(73) Assignee: Hortitrut North America, Inc., Estero, FL (US)

( * ) Notice: Subject to any disclaimer, the term of this patent is extended or adjusted under 35 U.S.C. 154(b) by 0 days.

(21) Appl. No.: 17/020,250

(22) Filed: Sep. 14, 2020

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499; A01H 5/08
See application file for complete search history.

*Primary Examiner* — Keith O. Robinson
(74) *Attorney, Agent, or Firm* — King IP Law; Joshua King

(57) ABSTRACT

The present invention relates to new and distinct cultivar of primocane-fruiting raspberry named 'PBB1473'. The new variety reliably provides balanced heavy crop load on both primocanes and floricanes, with jumbo, firm, glossy, orange-red colored conic fruits of loose adherence to the receptacle and which maintain size throughout harvest. Plants possess high vigor and produce high numbers of spawn. Improved resistance to yellow rust (*Phragmidium rubi-idaei*), field tolerance to Raspberry Bushy Dwarf Virus (RBDV) and *Phytophthora* root rot has been observed.

4 Drawing Sheets

Latin name of the genus and species of the plant claimed: *Rubus idaeus* L.

Variety denomination: 'PBB 1473'.

BACKGROUND AND SUMMARY

The new primocane-fruiting raspberry cultivar designated as 'PBB 1473' is described herein. Botanically known as *Rubus idaeus* L., this new variety resulted from a hand-pollinated cross of female parent 'Pacific Gema' (U.S. Plant Pat. No. 28,080P3), a release from the same program, and the male parent 'E10-22' (unpatented). Pollination occurred in April 2012 and seeds from this controlled cross were subsequently harvested, cleaned, germinated, and established as seedlings in spring 2013 in Watsonville, Calif., Santa Cruz County, USA.

'PBB 1473' was first identified in September 2014 in a substrate block where seedlings had individually been planted into 10 L pots in in Watsonville, Calif. This selection was first propagated asexually by crown division (of the original potted mother-plant) in December 2014 in Watsonville, Calif. The crown on the original plant was parted into basal cane pieces (approximately 15 cm long) with root attached, re-potted and placed inside of a screenhouse. The remaining roots were chilled for 4 weeks and planted inside into an onsite greenhouse to force adventitious shoots. Once rooted, individual adventitious shoots (propagules) were planted into a 10-plant plot. Harvest and postharvest data were collected from this larger plot of 'PBB 1473' for two years, from 2015 through 2017.

In January 2016, additional root pieces from the original mother-plant were planted into an on-site greenhouse. Two actively growing etiolated shoots were forced from roots, transplanted and potted. Once established, these young plants were sent to Lafayette, Oreg., USA, where vegetative material was explanted and established in vitro for micropropagation. Subsequent asexual propagation was done on-site in Watsonville, Calif. and, along with tissue-cultured plantlets, and 'PBB 1473' was evaluated extensively over the next several years for performance and genetic stability.

BRIEF SUMMARY OF THE INVENTION

The present cultivar, 'PBB 1473' offers many advantages over the existing cultivar and maternal parent, 'Pacific Gema' (U.S. Plant Pat. No. 28,080P3). Particularly for average berry weight, 'PBB 1473' (7.6 g) is noteworthy, for it is considered a jumbo berry and berriestend to weigh more than 'Pacific Gema' (5.3 g), on average. Yield of 'PBB 1473' (ranging from 23,997-29,764 kg/ha) is also greater than 'Pacific Gema' (ranging from 13,454-19,061 kg/ha), on average, due to its superior vigor, number of fruiting sites, and berry weight. Fruit color of 'PBB 1473' (RHS 34B) is non-darkening under postharvest evaluations, maintaining a fresh appearance. In contrast, 'Pacific Gema' (RHS 46A) darkens substantially during postharvest holding tests. Further, it has been observed that berries of 'PBB 1473' detach more easily from the receptacle than 'Pacific Gema', which aids in improved hand harvest efficiency. The heavier berry weight, improved yield, non-darkening color, and ease of fruit detachment offers significant advantages to growers, who require quality, fast picking speeds to maintain harvest efficiency.

In contrast to the unpatented male parent 'E10-22', the present cultivar is significantly greater in vigor, plant fitness, later in fruiting season, and offers longer fruiting laterals (personal observations of the inventor). In particular, the amount of suckers (spawn) that 'PBB 1473' produces is three-fold of its paternal parent (personal observations of the inventor). This improvement is of significant importance to growers, who rely upon the regenerative ability of suckers, in order to guarantee subsequent crops. Fruiting season of 'E10-22' generally begins on 12 July in primocanes for 'E10-22', and 1 August for 'PBB 1473'. For personal field observations, no quantitative measurements were collected comparing the male parent 'E10-22' and 'PBB 1473'.

Thus, these characteristics help define 'PBB 1473' as a new and distinct cultivar of primocane-fruiting raspberry. 'PBB 1473' may be recognized by its large, non-darkening berries that detach effortlessly and are borne from very long fruiting laterals, high vigor, late season, and strong suckering habit.

BRIEF DESCRIPTION OF THE PHOTOGRAPHS

Figure 1:
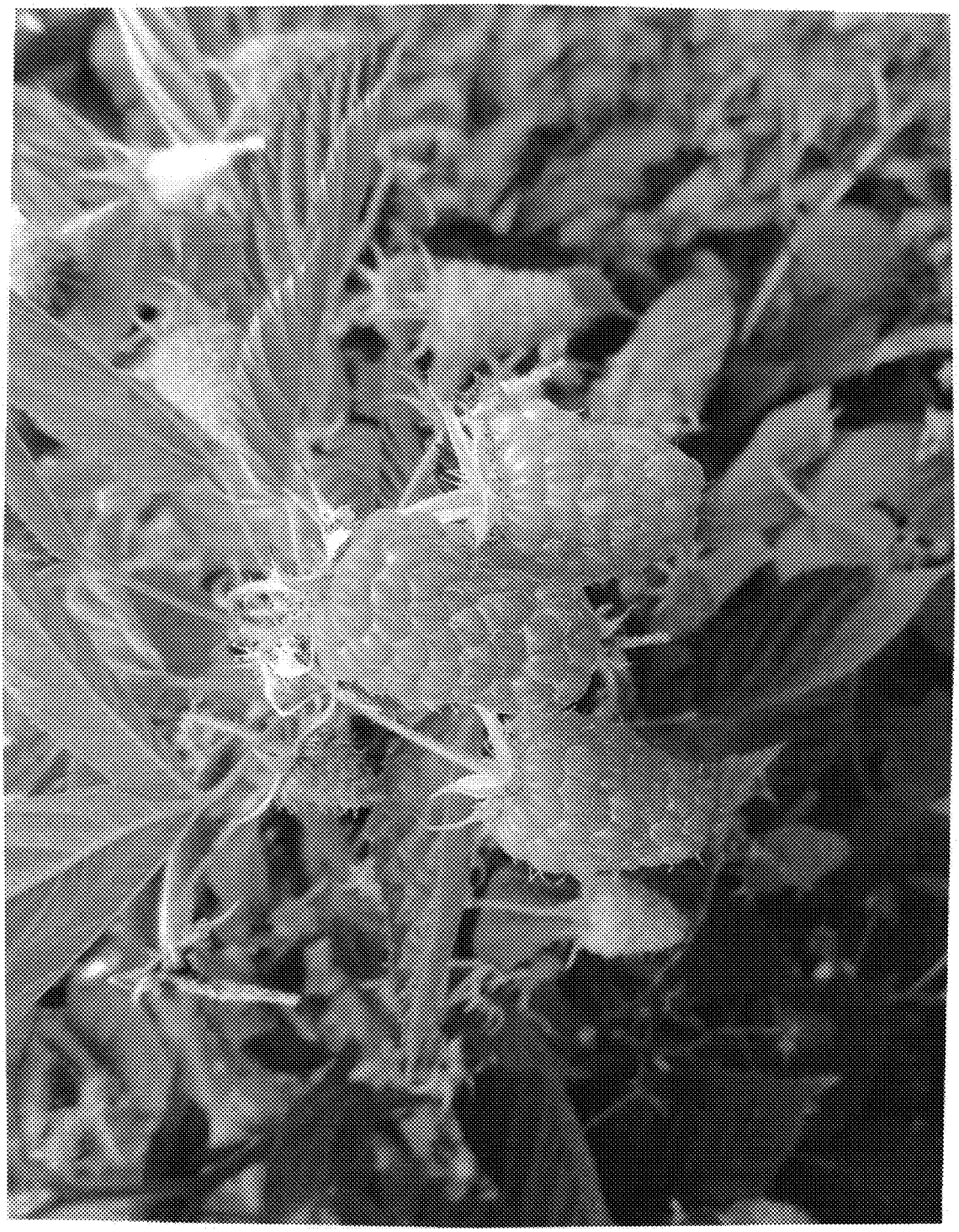
FIG. 1 is a photograph showing the fresh fruit color of raspberry cultivar 'PBB 1473'.
Figure 2:
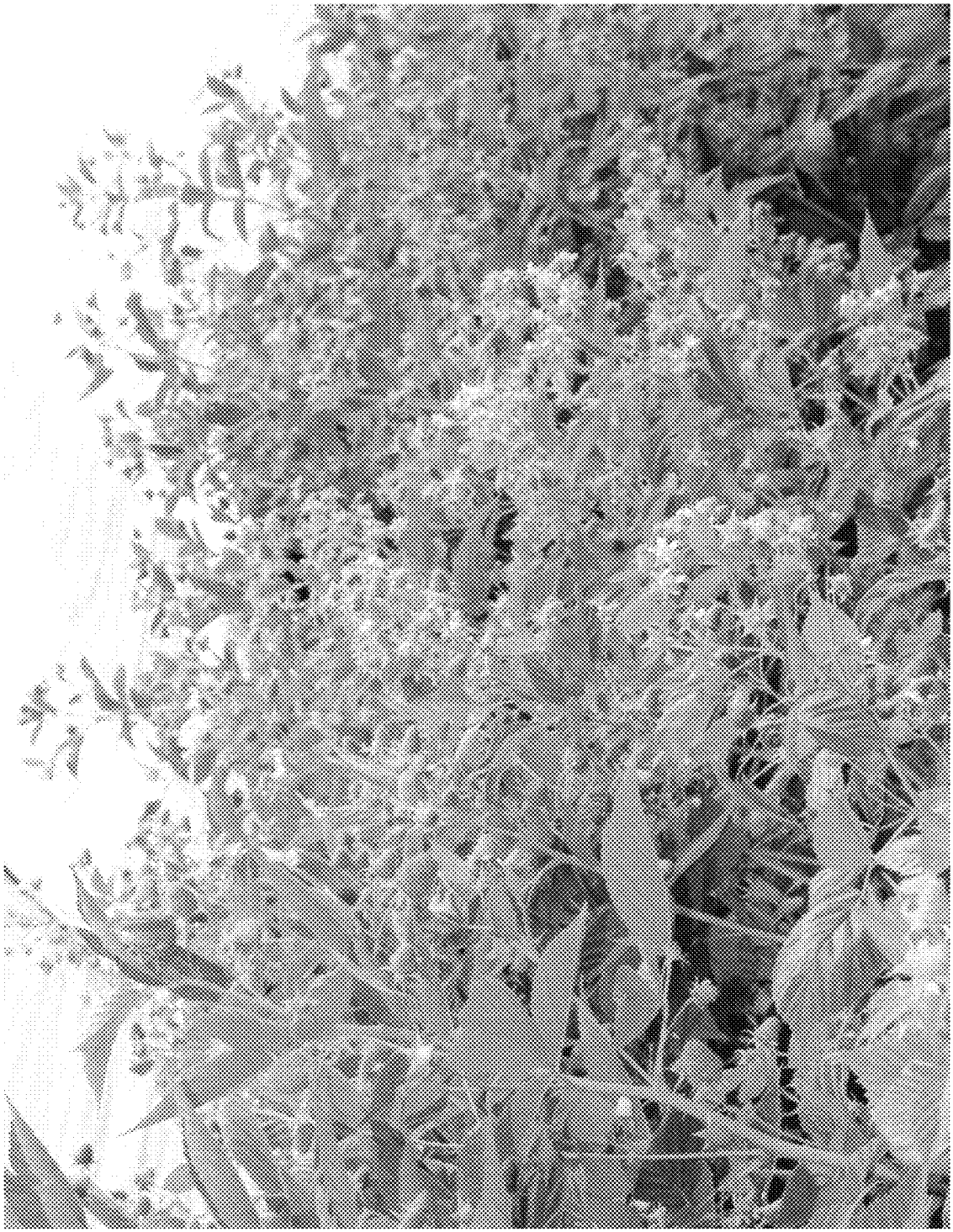
FIG. 2 is a photograph of 'PBB 1473' displaying cropload throughout its floricane canopy.
Figure 3:
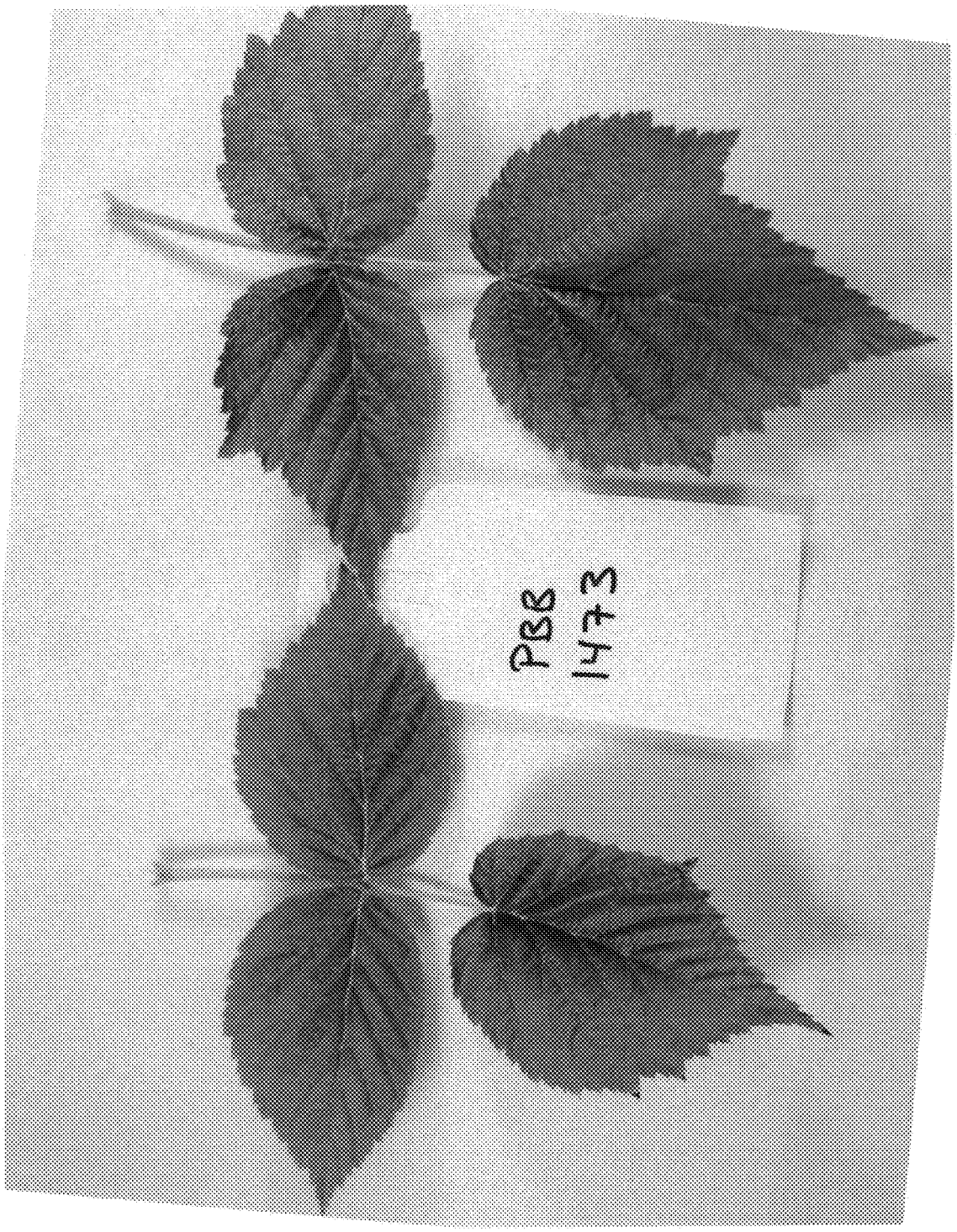

FIG. 3. Displays primocane leaf size and morphology of raspberry cultivar 'PBB 1473'.

Figure 4:
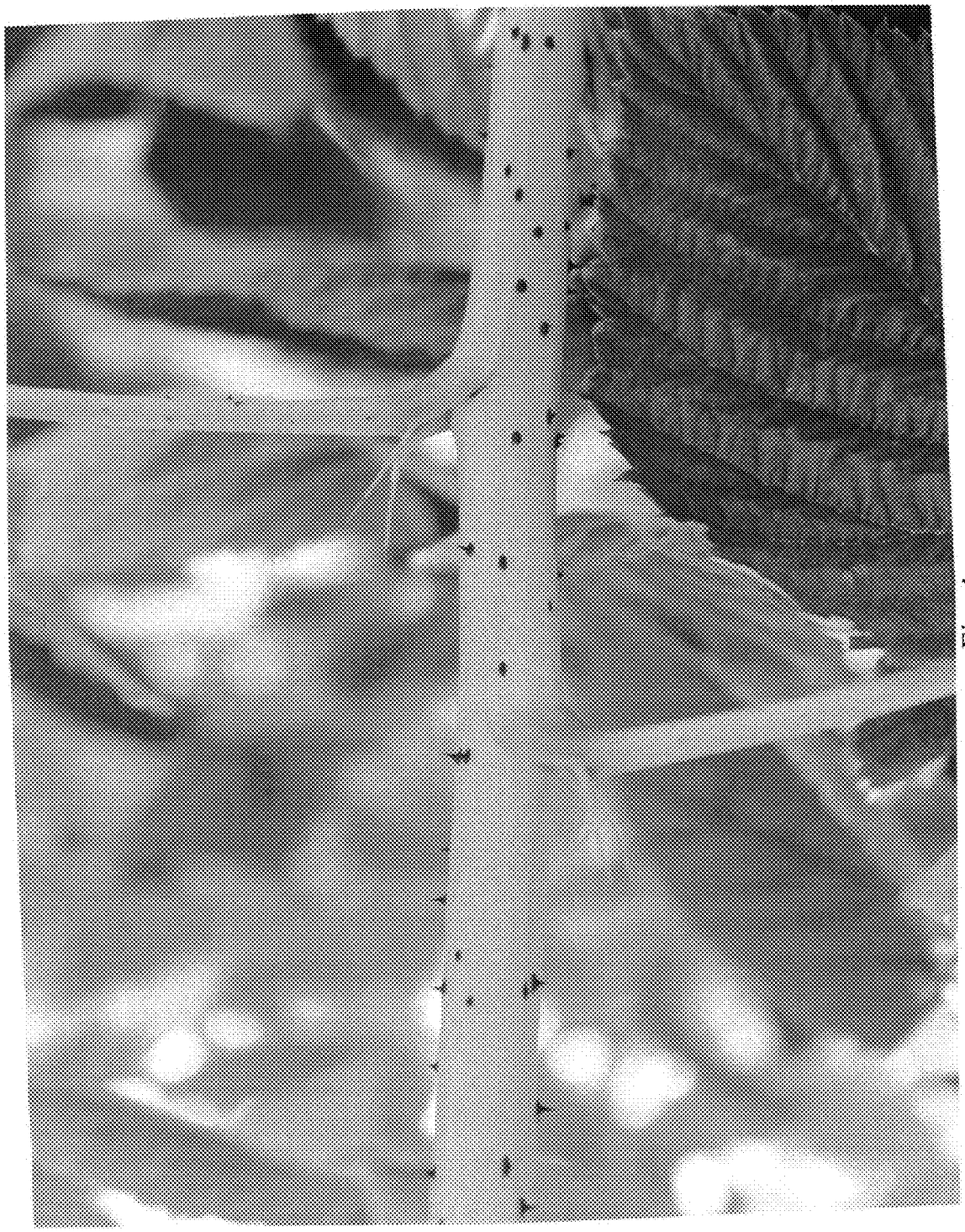

FIG. 4 is a photograph showing the cane and spine color of raspberry cultivar 'PBB 1473' on its primocanes.

DETAILED DESCRIPTION

Note: statements of characteristics herein represent exemplary observations of the cultivar herein and will vary depending on time of year, location, annual weather, etc.

Cultivar name: 'PBB 1473'.

Classification:

*Family*.—Rosaceae.

*Botanical name*.—*Rubus idaeus* L.

*Common name*.—Raspberry.

Parentage:

*Female parent*.—'Pacific Gema'.

*Male parent*.—'E10-22'.

Growing location for the observations herein: Watsonville, Calif., USA.

Time of year (season): Early summer for floricanes, and late summer for primocanes.

Age of plants used for this discussion: Crown age of about 2 years; floricane age 18 months; primocane age 8 months.

Age of plants used for the photographs in the figures: Crown age of about 2 years; floricane age 18 months; primocane age 8 months.

Type of greenhouse covering or growing structure, or field: High tunnel over substrate-grown plants.

Light: Natural.

Color terminology refers to The R.H.S. Colour Chart, Royal Horticultural Society, Fifth Edition, London, United Kingdom (2007).

Observations for floricanes herein were made in June 2019. Observations for primocanes herein were made in September 2019.

Plant:

*Form/shape*.—Vase.

*Growth habit*.—Erect.

*Height*.—236 cm, as measured from cane base to apex.

*Spread*.—75 cm as measured from terminal leaflet tip to terminal leaflet tip.

*Propagation methods*.—Tissue culture.

*Time to initiate and develop roots*.—24 days.

*Root description*.—Fibrous.

Primocanes:

*Cane diameter*.—Base: 1.2 cm|Middle: 1.0 cm|Tip: 0.5 cm.

*Cane length*.—2.3 m.

*Number of node per cane*.—40.

*Internode length*.—Base: 8.4 cm|Middle: 7.5 cm|Tip: 4.2 cm.

*Number of canes/hill*.—5 to 8.

*Cane color*.—Base — RHS 144B; Middle and tip — RHS 184A.

*Spines*.—Present.

*Spine density*.—Base: 9.3/cm$^2$|Middle: 6.7/cm$^2$|Tip: 5.3/cm$^2$.

*Spine shape*.—Acuminate.

*Spine length*.—0.2 cm.

*Spine width*.—0.3 cm.

*Spine apex descriptor*.—Acuminate.

*Spine color*.—RHS N186A.

*Vegetative bud shape*.—Rounded.

*Vegetative bud length*.—0.8 cm.

*Vegetative bud diameter* (*base*).—0.4 cm.

*Vegetative bud diameter* (*tip*).—0.1 cm.

*Vegetative bud color*.—RHS 144B.

Floricanes:

*Cane diameter*.—Base — 1.0 cm|Middle — 1.2 cm|Tip — 0.8 cm.

*Cane length*.—80 cm (pruned to this height in February 2019).

*Number of nodes per cane*.—19.

*Internode length*.—Base — 2.6 cm|Middle — 4.6 cm|Tip — 5.4 cm.

*Cane color*.—Lower Cane — RHS 197D|Upper Cane — RHS 165A (undertone) RHS 165B. (overtone).

*Spines*.—Present. Spine density: Base: 13/cm$^2$|Middle: 6/cm$^2$|Tip: /cm$^2$. Spine shape: Acuminate. Spine length: 0.1 cm. Spine width: 0.03 cm. Spine apex descriptor: Acuminate. Spine color: RHS 197D.

*Reproductive bud shape*.—Rounded.

*Reproductive bud length*.—0.7 cm.

*Reproductive bud diameter* (*base*).—0.4 cm.

*Reproductive bud diameter* (*tip*).—0.1 cm.

*Reproductive bud color*.—RHS 144B.

*Reproductive bud texture*.—Pubescent.

*Winter hardiness*.—Unknown outside of USDA Hardiness Zone 9b (Watsonville, Calif.). This cultivar is best adapted to the mild coastal conditions of California.

*Drought/heat tolerance*.—Pollen viability and fruit quality of raspberry generally begins to decline above 30° C. This is consistent with observations of 'PBB 1473'. Raspberries are generally not drought tolerant, and 'PBB 1473' has not been tested in unirrigated plots.

Leaves:

*Complete leaf*.—Length: 25.2 cm. Width: 19.3 cm. Number of leaflets: 3.

*Terminal leaflet*.—Size — Length: 10.1 cm. Width: 8.9 cm. Length/Width ratio: 1.13 cm. Leaf shape of apex: Acuminate. Leaf shape of base: Cordate. Leaf margin: Serrate. Leaf texture: Mild interveinal puckering. Number of serrations per leaf: 66 serrations. Leaf shape of serrations: Flexuous — Flexuous. Leaf color: Upper Surface: RHS N137A. Lower Surface: RHS N138C. Leaf venation pattern: Palmate. Leaf venation color: Upper surface: RHS N144A. Lower surface: RHS N139D. Leaf pubescence density: Present on underside only; low density. Color of leaf pubescence: RHS N138C. Shape of leaf in cross-section: Oval. Number of leaflets/leaf: Primocane: 3-5 Floricane: 3. Interveinal blistering within leaf: Present, mild. Leaf rugosity: Medium. Leaf glossiness: Matte (upper and lower surface).

*Primocane leaves*.—Petiole length: 5.5 cm. Petiole diameter: 0.3 cm. Petiole Color: Upper: RHS 145A (undertone); RHS176A (overtone). Lower: RHS 145C. Rachis length: 11.8 cm (compound leaf). Rachis color: RHS 145C. Stipule length: 0.8 cm. Stipules per leaf: 2. Stipule Width: 0.05 cm. Stipule Color: Upper Surface: RHS 146C (undertone); RHS 174A (overtone). Lower Surface: RHS 144A.

*Terminal leaflet*.—Length: 12.2 cm. Width: 9.4 cm. Rachis length: 4.0 cm.

*Distal lateral leaflet*.—Length: N/A. Width: N/A. Petiolule length: N/A.

*Basal lateral leaflet*.—Length: 9.9 cm. Width: 6.6 cm. Petiolule length: 0.2 cm.

*Floricane leaves*.—Petiole length: 5.5 cm. Stipule length: 0.4 cm. Stipules per leaf: 2. Stipule Width: 0.09 cm. Stipule Color: RHS N144B. Color Upper surface: RHS N137A. Lower surface: RHS 138C.

*Terminal leaflet*.—Length: 9.6 cm. Width: 7.4 cm. Rachis length: 2.8 cm. Distal lateral leaflet: Length: N/A. Width: N//A.

*Petiolule*.—Length: N/A. Diameter: N/A. Color: N/A.

*Basal lateral leaflet*.—Length: 8.3 cm. Width: 5.1 cm.

*Petiolule*.—Nearly sessile. Length: 0.19 cm. Diameter: 0.15. Color: Upper: RHS 145B. Lower: RHS 145B.

Flowers:

*Time of flowering* (50% *of plants at first flower*).—Approximately 170 days after planting (on primocanes).

*Flower size*.—Length: 0.96 cm. Diameter: 2.8 cm.

*Fragrance*.—None.

*Peduncle*.—Length: 4.9 cm. Diameter: 0.15 cm. Color: RHS 145A. Pubescence: Puberulent. Texture: Small prickles present.

*Perianth*.—Flowering trusses shape: Truncate.

*Petals*.—Color: Upper — RHS 157D|Lower — RHS 157C. Number per flower: 5 petals. Shape: Obovate. Length: 0.8 cm. Width: 0.4 cm. Apex descriptor: Emarginate. Base Descriptor: Truncate. Margin descriptor: Entire. Texture: Smooth with visible striations.

*Sepals*.—Quantity: 5 sepals. Length: 0.7 cm. Width: Base — 0.4 cm|Mid — 0.2 cm|Tip — 0.09 cm. Color: RHS 144D. Apex descriptor: Acuminate. Margin descriptor: Entire. Texture: Pubescent.

*Pedicel*.—Color: RHS 144A. Length: 3.4 cm. Diameter: 0.1 cm.

Reproductive organs: Self-fertile: Yes.

*Male*.—Stamen Number: 123. Filament — Length: 0.45 cm. Diameter: 0.02 cm. Color: RHS 155C. Anther — Length: 0.02 cm. Diameter: 0.06 cm. Color: RHS 165D. Pollen — Color: RHS 199A. Amount: Moderate.

*Female*.—Style — Length: 0.04 cm. Diameter: 0.01 cm. Color: RHS 157C. Stigma — Length: 0.09 cm. Diameter: 0.007 cm. Color: RHS 155D. Ovary — Length: 0.01 cm. Diameter: 0.07 cm. Color: N144D.

Fruit:

*Predominant shape*.—Elongated Conical.

*Weight* (*g*).—6.2 g.

*Length*.—3.1 cm.

*Width*.—Base — 2.2 cm|Mid — 1.6 cm|Tip — 1.1 cm.

*Length/width ratio*.—1.4.

*Receptacle*.—Length: 1.6 cm. Diameter: Base — 0.7 cm|Mid — 0.5 cm|Tip — 0.2 cm. Color: RHS 158A.

*Drupelet*.—Length: 0.6 cm. Diameter: 0.3 cm. Number: 110. Weight: 0.05 g.

*Fruit color*.—External: RHS 34B. Internal: RHS 31C.

*Firmness of skin*.—Firm.

*Firmness of flesh*.—Firm.

*Hollow center*.—Present.

*Number of fruit per node*.—15-17.

*Time of ripening* (50% *of plants with first fruit*).—210 days after planting, on average.

*Time of fruiting*.—Spring to summer on floricanes; late summer and early autumn on primocanes.

*Type of bearing*.—Remontant.

*Fruit yield*.—22,500 lb/a, on average.

*Average brix*.—9.6.

*Typical market use*.—Fresh.

*Keeping quality*.—Excellent.

*Shipping quality*.—Excellent.

Pest and disease resistance: 'PBB 1473' shows resistance to yellow rust (*Phragmidium rubi-thunbergii*), a common fungal disease under commercial conditions. 'PBB 1473' has exhibited field tolerance to Raspberry Bushy Dwarf Virus (RBDV) and *Phytophthora* root rot.

What is claimed is:

1. A new and distinct cultivar of Raspberry plant named 'PBB 1473' as described and shown herein.

* * * * *